(12) United States Patent
Elliott et al.

(10) Patent No.: US 11,763,922 B2
(45) Date of Patent: Sep. 19, 2023

(54) ELECTRONIC CASE REPORTING TRANSFORMATION TOOL

(71) Applicant: Michigan Health Information Network Shared Services, East Lansing, MI (US)

(72) Inventors: Brandon Gene Elliott, Lansing, MI (US); Jacob Scott Davis, Laingsburg, MI (US)

(73) Assignee: Michigan Health Information Network Shared Services, East Lansing, MI (US)

( * ) Notice: Subject to any disclaimer, the term of this patent is extended or adjusted under 35 U.S.C. 154(b) by 113 days.

(21) Appl. No.: 16/748,912

(22) Filed: Jan. 22, 2020

(65) Prior Publication Data

US 2021/0225470 A1 Jul. 22, 2021

(51) Int. Cl.
*G16H 15/00* (2018.01)
*G06Q 10/10* (2023.01)
*G16H 10/60* (2018.01)

(52) U.S. Cl.
CPC ............. *G16H 15/00* (2018.01); *G06Q 10/10* (2013.01); *G16H 10/60* (2018.01)

(58) Field of Classification Search
CPC ......... G16H 15/00; G16H 10/60; G06Q 10/10
USPC ........................................................ 705/2–4
See application file for complete search history.

(56) References Cited

U.S. PATENT DOCUMENTS

| 3,384,033 | A | * | 5/1968 | Ruff | ........................ | B60L 15/32 |
| | | | | | | 105/61 |
| 2013/0318111 | A1 | * | 11/2013 | Davis | ..................... | G16H 40/20 |
| | | | | | | 707/756 |

OTHER PUBLICATIONS

Electronic Case Reporting (eCR) Implementation Guide, version 13, issued by the Michigan Health Information Network on May 4, 2018 (available at https://mihin.org/wp-content/uploads/2018/06/MiHIN-eCR-Implementation-Guide-v17-06-19-18.pdf) (Year: 2018).*

(Continued)

*Primary Examiner* — Mark Holcomb
(74) *Attorney, Agent, or Firm* — Honigman LLP

(57) ABSTRACT

A method of electronically reporting a reportable condition includes receiving a first document associated with a first type of a Consolidated-Clinical Document Architecture (C-CDA) standard. The first document includes patient information associated with a patient treated by a healthcare provider (HCP). The method also includes parsing the first document into a plurality of patient information fields and determining whether any of the plurality of patient information fields in the parsed first document include a reportable condition. When at least one patient information field of the plurality of patient information fields includes the reportable condition, the method also includes generating a second document associated with a second type of the C-CDA standard and including the reportable condition.

26 Claims, 7 Drawing Sheets

(56) References Cited

OTHER PUBLICATIONS

HL7 CDA® R2 Implementation Guide: Public Health Case Report, Release 2: the Electronic Initial Case Report (eICR), Release 1, STU Release 1.1, released by HL7 International in Jan. 2017 (available at http://www.hl7.org/implement/standards/product_brief.cfm?product_id=436) (Year: 2017).*

Dinh Tuyen Hoang, In Keun Lee, Dosam Hwang, Version-Compatible HL7 Parser Based on Object-Oriented Design, Vietnam Journal of Computer Science, doi: 10.1142/S2196888819500258 (Year: 2019).*

\* cited by examiner

ELECTRONIC CASE REPORTING TRANSFORMATION TOOL

TECHNICAL FIELD

This disclosure relates to an electronic case reporting transformation tool.

BACKGROUND

Infectious diseases kill more than 17 million people around the world each year and can be transported in several ways, including through human contact, animals and insects, food, water, or through organisms in the environment. As an important component of overall public health, healthcare providers are obligated to report specific conditions to assist public health agencies in managing the outbreaks of infectious diseases such as Ebola or Measles, as well as to monitor more routine trends that need to be investigated and managed by public health officials to protect the public from infection. Currently, upward of 90 conditions are required by law to be reported in every state and territory in the United States. The modern adoption of electronic health record (EHR) reporting can assist in providing fast and reliable reporting systems to prevent the ability for infectious diseases to spread rapidly through the diverse number of possible ways.

SUMMARY

One aspect of the disclosure provides a method for electronically reporting a reportable condition. The method includes receiving, at data processing hardware, a first document associated with a first type of a Consolidated-Clinical Document Architecture (C-CDA) standard. The first document includes patient information associated with a patient treated by a healthcare provider (HCP). The method also includes parsing, by the data processing hardware, the first document into a plurality of patient information fields, and determining, by the data processing hardware, whether any of the plurality of patient information fields in the parsed first document include a reportable condition. When at least one patient information field of the plurality of patient information fields includes the reportable condition, the method also includes generating, by the data processing hardware, using the first document, a second document associated with a second type of the C-CDA standard.

Implementations of the disclosure may include one or more of the following optional features. After generating the second document, the method may include transmitting, by the data processing hardware, the second document to a public health agency (PHA) computing device associated with a PHA. In some implementations, the second document includes the reportable condition and the second type of the C-CDA standard is different than the first type of the C-CDA standard. The PHA computing device is configured to process the second document to extract the reportable condition from the second document. In some implementations, the first type of the C-CDA standard includes a Continuity of Care Document (CCD) generated by an electronic health record (EHR) system, wherein the EHR system is configured to: receive the patient information from a HCP device associated with the patient, the patient information input to the HCP device by the HCP; and generate the CCD based on the received patient information. In other implementations, the first type of the C-CDA standard includes a patient care document generated by the EHR system, wherein the EHR system is configured to: receive the patient information from the HCP device associated with the patient, the patient information input to the HCP device by the HCP; and generate the patient care document based on the received patient information. Moreover, the PHA computing device may be unable to process documents associated with the first type of the C-CDA standard. The second type of the C-CDA standard may include an Electronic Initial Case Report (eICR).

In some examples, generating, using the first document, the second document associated with the second type of the C-CDA standard includes identifying required patient information from a first portion of the plurality of patient information fields in the parsed first document; identifying unnecessary patient information from a second portion of the plurality of patient information fields in the parsed first document; and generating the second document by populating required fields specified by the second type of the C-CDA standard with the required patient information identified from the first portion of the plurality of patient information fields in the parsed first document. The required patient information is required for inclusion in documents associated with the second type of the C-CDA standard, while the unnecessary patient information is omitted from documents associated with the second type of the C-CDA standard. In these examples, the method may also include determining, by the data processing hardware, that the second type of the C-CDA standard specifies one or more fields to be created in documents associated with the second type of the C-CDA standard. Here, for each field, the method may include: determining, by the data processing hardware, from a third portion of the plurality of patient information fields in the parsed first document, whether corresponding optional patient information exists for inclusion in the corresponding field; and one of: when the corresponding optional patient information exists, populating, by the data processing hardware, the corresponding field specified by the second type of the C-CDA standard with the corresponding optional patient information; or when the corresponding optional patient information does not exist, populating, by the data processing hardware, the corresponding field specified by the second type of the C-CDA standard with blank data.

In some implementations, determining whether any of the plurality of patient information fields in the parsed first document include the reportable condition includes obtaining a list of reportable conditions from a reportable condition datastore in communication with the data processing hardware and determining that the at least one patient information field of the plurality of patient information fields includes one of the reportable conditions in the list of reportable conditions obtained from the reportable condition datastore. In these implementations, the list of reportable conditions is specified by the PHA. For instance, the PHA computing device may input the list of reportable conditions to the reportable condition datastore directly, or the PHA computing device may provide the list of reportable conditions to the data processing hardware for inclusion to the reportable condition datastore.

The at least one patient information field of the plurality of patient information fields may include the reportable condition when the at least one patient information field includes a diagnoses code indicative of the reportable condition and/or when the at least one patient information field includes a laboratory code indicative of the reportable condition. The laboratory code may include a Laboratory Observation Identifiers Names and Codes (LOINC) code.

Additionally, the at least one patient information field of the plurality of patient information fields may include the reportable condition when the at least one patient information field includes a Systematized Nomenclature of Medicate (SNOMED) code indicative of the reportable condition.

In some examples, prior to generating the second document, the method also includes determining, by the data processing hardware, whether any of the plurality of patient information fields in the parsed first document are missing corresponding required patient information required for generating documents associated with the second type of the C-CDA standard, and when one or more of the plurality of patient information fields in the parsed first document are missing the corresponding required patient information, ceasing, by the data processing hardware, the generating of the second document associated with the second type of the C-CDA standard. Moreover, when the one or more of the plurality of patient information fields in the parsed first document are missing the corresponding required patient information, the method may also include transmitting, by the data processing hardware, a failed conversion message to a HCP computing device associated with the HCP. The failed conversion message may inform the HCP that the second document associated with the second type of the C-CDA standard and including the reportable condition could not be generated.

Another aspect of the disclosure provides a system for electronically reporting a reportable condition. The system includes data processing hardware and memory hardware in communication with the data processing hardware and storing instructions that when executed by the data processing hardware cause the data processing hardware to perform operations. The operations include receiving a first document associated with a first type of a Consolidated-Clinical Document Architecture (C-CDA) standard. The first document includes patient information associated with a patient treated by a healthcare provider (HCP). The operations also includes parsing the first document into a plurality of patient information fields and determining whether any of the plurality of patient information fields in the parsed first document include a reportable condition. When at least one patient information field of the plurality of patient information fields includes the reportable condition, the operations also include generating, using the first document, a second document associated with a second type of the C-CDA standard. The second document includes the reportable condition and the second type of the C-CDA standard is different than the first type of the C-CDA standard.

This aspect may include one or more of the following optional features. After generating the second document, the operations may also include transmitting the second document to a public health agency (PHA) computing device associated with a PHA. The PHA computing device is configured to process the second document to extract the reportable condition from the second document. In some implementations, the first type of the C-CDA standard includes a Continuity of Care Document (CCD) generated by an electronic health record (EHR) system, wherein the EHR system is configured to: receive the patient information from a HCP device associated with the patient, the patient information input to the HCP device by the HCP; and generate the CCD based on the received patient information. In other implementations, the first type of the C-CDA standard includes a patient care document generated by the EHR system, wherein the EHR system is configured to: receive the patient information from the HCP device associated with the patient, the patient information input to the HCP device by the HCP; and generate the patient care document (other than a CCD) based on the received patient information. In some examples, the patient care document includes a Continuity of Care Record (CCR). Moreover, the PHA computing device may be unable to process documents associated with the first type of the C-CDA standard. The second type of the C-CDA standard may include an Electronic Initial Case Report (eICR).

In some examples, generating, using the first document, the second document associated with the second type of the C-CDA standard includes identifying required patient information from a first portion of the plurality of patient information fields in the parsed first document; identifying unnecessary patient information from a second portion of the plurality of patient information fields in the parsed first document; and generating the second document by populating required fields specified by the second type of the C-CDA standard with the required patient information identified from the first portion of the plurality of patient information fields in the parsed first document. The required patient information is required for inclusion in documents associated with the second type of the C-CDA standard, while the unnecessary patient information is omitted from documents associated with the second type of the C-CDA standard. In these examples, the operations may also include determining that the second type of the C-CDA standard specifies one or more fields from the first type of the C-CDA standard to be created in documents associated with the second type of the C-CDA standard. Here, for each field, the operations may include: determining, from a third portion of the plurality of patient information fields in the parsed first document, whether corresponding patient information exists for inclusion in the corresponding field; and one of: when the corresponding optional patient information exists, populating the corresponding field specified by the second type of the C-CDA standard with the corresponding optional patient information; or when the corresponding optional patient information does not exist, populating the corresponding field specified by the second type of the C-CDA standard with blank data.

In some implementations, determining whether any of the plurality of patient information fields in the parsed first document include the reportable condition includes obtaining a list of reportable conditions from a reportable condition datastore in communication with the data processing hardware and determining that the at least one patient information field of the plurality of patient information fields includes one of the reportable conditions in the list of reportable conditions obtained from the reportable condition datastore. In these implementations, the list of reportable conditions is specified by the PHA. For instance, the PHA computing device may input the list of reportable conditions to the reportable condition datastore directly, or the PHA computing device may provide the list of reportable conditions to the data processing hardware for inclusion to the reportable condition datastore.

The at least one patient information field of the plurality of patient information fields may include the reportable condition when the at least one patient information field includes a diagnoses code indicative of the reportable condition and/or when the at least one patient information field includes a laboratory code indicative of the reportable condition. The laboratory code may include a Laboratory Observation Identifiers Names and Codes (LOINC) code. Additionally, the at least one patient information field of the plurality of patient information fields may include the reportable condition when the at least one patient information field includes a Systematized Nomenclature of Medicate (SNOMED) code indicative of the reportable condition.

In some examples, prior to generating the second document, the operations also includes determining whether any of the plurality of patient information fields in the parsed first document are missing corresponding required patient information required for generating documents associated with the second type of the C-CDA standard, and when one or more of the plurality of patient information fields in the parsed first document are missing the corresponding required patient information, ceasing the generating of the second document associated with the second type of the C-CDA standard. Moreover, when the one or more of the plurality of patient information fields in the parsed first document are missing the corresponding required patient information, the operations may also include transmitting a failed conversion message to a HCP computing device associated with the HCP. The failed conversion message may inform the HCP that the second document associated with the second type of the C-CDA standard and including the reportable condition could not be generated.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
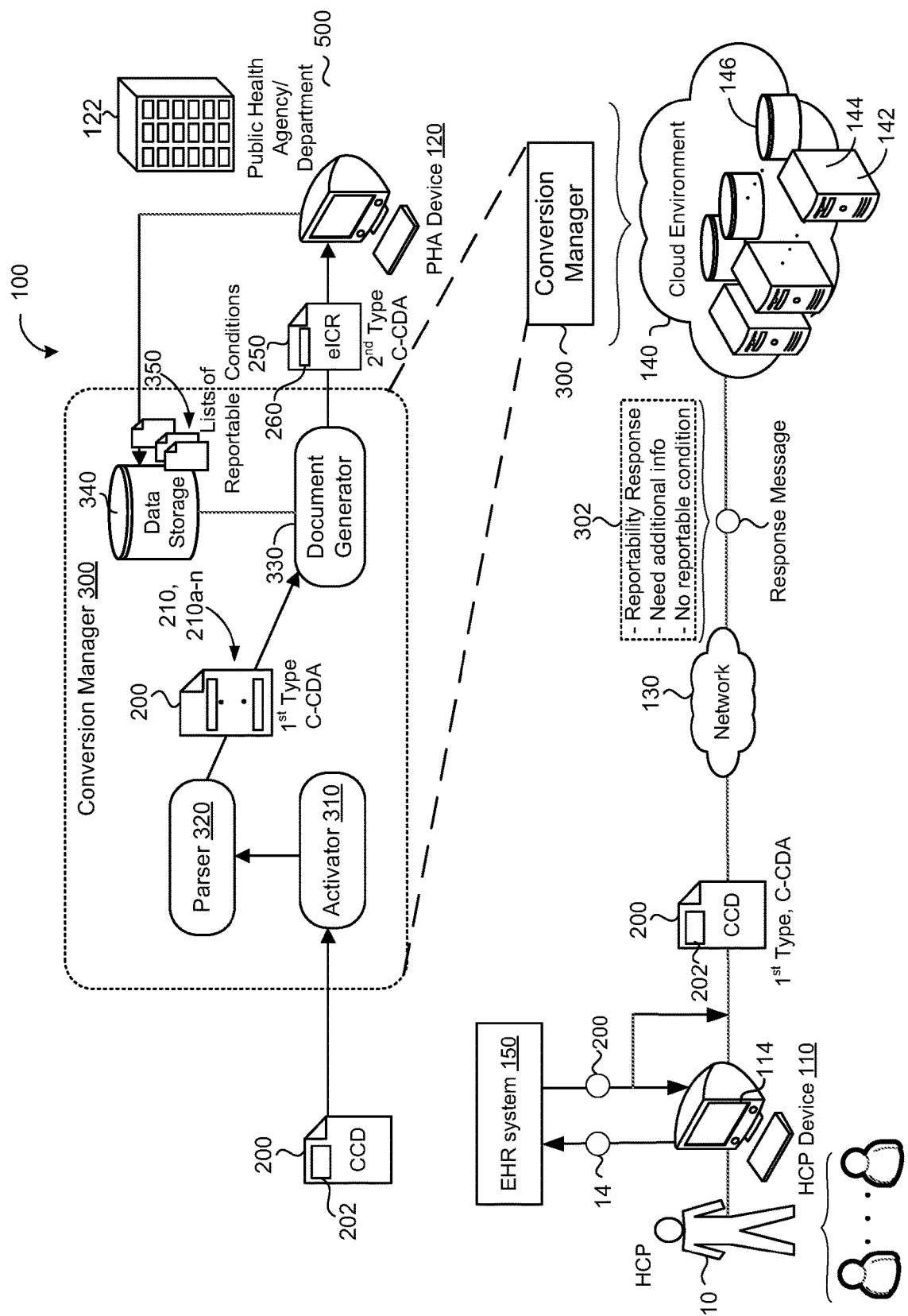
FIG. 1 is a schematic view of an electronic case reporting system.

To assist public health officials in protecting the public health from infectious diseases and other infections, states and territories have enacted laws that require healthcare providers to report specific conditions identified in patients seeking treatment. Currently, upward of 90 conditions are required by law to be reported to public health agencies in every state and territory to assist the public health agencies in managing these "reportable conditions" in their surveillance systems. As used herein, the term "reportable condition" refers to any infectious disease, infection, or other condition required by law to be reported to an agency, government, institution, or other entity responsible for documenting, monitoring, and/or managing the underlying infectious disease, infection, or other condition. Here, each "reportable condition" can be added to list of reportable conditions that healthcare professionals can access to determine which conditions identified in patients (or conditions that patients may be suspected to have or at risk of contracting) are required to be reported and to which agency/ entity should receive the report. Moreover, the list of "reportable conditions" can be updated at any time. At the same time, a "reportable condition" can include specific diagnosis codes, laboratory codes, or other characteristics indicative of an underlying infectious disease, infection, or other condition that is required by law to be reported for public health awareness. As used herein, the phrase "required by law" refers to any federal regulation, state legislation, or state level administrative rule or directive that specifies reportable conditions and proper public health agencies that healthcare providers are required to report to when any specified reportable condition is identified in patients under the supervision of the HCPs. Generally, healthcare providers are required to report communicable diseases so that outbreaks can be managed, more routine trends can be investigated and managed, the public can be protected from infection, treatment and education can be provided to impact populations and providers, preventive measures can be enacted, long-term success efforts can be measured, and research into causes and cures can be more exact.

Conventionally, when a healthcare provider (HCP) (e.g., physicians, clinical laboratories, hospitals, dentists, etc.) identifies or suspects that a patient has a reportable condition, the HCP reports the condition to the necessary public health agency (PHA) by manually filling out a written report documenting the reportable condition and faxing or mailing the written report to the necessary PHA. The HCP may also simply report the condition via a telephone call to the necessary PHA. This is a very time-consuming and burdensome process for the HCP that takes time away from the HCP for caring for other patients, while at the same time, leads to slow response times in reporting reportable conditions that can lead to dangerous disease outbreaks. Moreover, a busy HCP may not have the time to immediately fill out these special forms and/or make the phone calls, thereby inhibiting PHAs from acting promptly to manage outbreaks. Even more worrisome, due to a simple oversight, an HCP may altogether forget to report the condition. Obviously, such occurrences are a detriment to public health because the PHA is not able to effectively manage infectious diseases that are not reported promptly or that never get reported.

The adoption of modern certified electronic health record (EHR) and electronic medical record (EMR) technologies can be used to effectively identify patient populations with reportable conditions, and support electronically sending files using the Consolidated-Clinical Document Architecture (C-CDA) standard in a manner that is more secure than sending documents via fax. Generally, the C-CDA standard specifies that a document must include a mandatory textual part, which ensures human interpretation of the contents of the document, and an optional structured part for software processing. Here, the structured part of the C-CDA document is based on Health Level Seven (HL7) Reference Information Model (RIM) and provides a framework for referring to concepts from coding systems, such as Systematized Nomenclature of Medicate (SNOMED) codes, Laboratory Observation Identifiers Names and Codes (LOINC) codes, as well as medical diagnosis codes used by HCPs for diagnosing treated patients.

One type of document implementing the C-CDA standard is an electronic Initial Case Report (eICR) document which is accepted as a national standard for providing electronic Case Reporting (eCR) capability for reporting cases of infectious diseases to necessary PHAs. Generally, the eICR document provides automated generation and transmission of reportable conditions from the patient's EHR to necessary PHAs for review and action, thereby alleviating the HCPs from the time-sensitive manual processes (e.g., written reports, fax, or mail) to fulfill their requirement in reporting cases of infectious diseases to the PHAs. Thus, the eICR document digitally sends potential disease cases flagged in an EHR to the PHA to improve routine outbreak management of infectious diseases. While EHR vendors are available for producing eICR documents for use by HCPs in reporting reportable conditions to necessary PHAs, HCPs are slow to adopt the standard (e.g., HL7 CDA R2) for producing eICR documents since there are no current government mandates for compliance or funding, thereby requiring HCPs seeking to adopt the eICR standard to incur additional costs at their own expense.

Another type of document implementing the C-CDA standard is a Continuity of Care Document (CCD) used by HCPs for electronically exchanging patient summaries. In order to be certified under the United States (U.S.) federal program for receiving incentives for the adoption EHRs, HCPs must be able to generate a CCD that includes sections of allergies, medications, problems, and laboratory results, in addition to patient header information. In short, a vast majority of HCPs use EHR vendors that are already capable of routinely generating, updating, and exchanging CCDs for treated patients due to the certification requirements for adopting the use of EHRs. The CCD includes a vast number of patient data fields related to the respective patient, some of which include content required by standard for inclusion in an eICR document for reporting infectious diseases.

Implementations herein are directed toward methods and systems for providing interoperable electronic case reporting capability between healthcare providers (HCPs) and public health reporting agencies (PHAs) by leveraging CCD documents automatically created after patient encounters, which may include a patient discharge, for conversion into eICR documents for electronically reporting "reportable conditions" (e.g., infectious diseases, infections, conditions). As used herein, a "public health agency" can be any agency, department, institution, or government entity responsible for documenting, monitoring, and/or managing "reportable conditions" identified by HCPs. Thus, an HCP that determines/suspects that a patient has a reportable condition, can simply send a CCD that is automatically generated for the patient after patient encounters, which may include a patient discharge, to an eICR transformation tool (e.g., conversion manager 300 of FIG. 1) that is configured to identify the reportable condition in the CCD and generate the necessary eICR document in compliance with mandated standards. Thereafter, the eICR document is automatically sent electronically to an appropriate public health department (e.g., PHA) that has appropriate surveillance systems for outbreak management of infectious diseases. Advantageously, cases of infectious diseases can be accurately and quickly reported to appropriate PHAs using already created CCD documents without requiring the HCPs to undertake the time-sensitive, and less secure, process of manually filling out reports and sending the reports to the PHAs via fax or mail.

Referring to FIG. 1, in some implementations, an electronic case reporting (eCR) system 100 includes a healthcare professional (HCP) computing device 110 associated with a HCP 10, who may communicate, via a network 120, with a remote system 140 and an electronic health record (EHR) system 150. The remote system 140 may be a distributed system (e.g., cloud computing environment) having scalable/elastic resources 142. The resources 142 include computing resources 144 (e.g., data processing hardware) and/or storage resources 146 (e.g., memory hardware). In some implementations, the remote system 140 executes a conversion manager 300 configured to receive a first document 200 associated with a first type of a Consolidated Clinical Document Architecture (C-CDA) standard from the HCP device 110 or the EHR system 150, determine whether the first document 200 includes any reportable conditions, and when the first document 200 includes at least one reportable condition, use the first document 200 to generate a second document 250 associated with a second type of the C-CDA standard. As will become apparent, the conversion manager 300 enables HCPs to automatically send comprehensive electronic case reports about infectious diseases as part of their daily routine. For instance, certified EHR technology provides documentation that may contain clinical information pertaining to patients with reportable conditions, and may support securely sending Continuity of Care Documents (CCDs) through Consolidated Clinical Document Architecture (C-CDA) files.

The HCP 10 may treat patients 12, 12a—n seeking treatment for conditions the patients 12 are experiencing. For instance, the HCP 10 may be a physician employed by a medical clinic or hospital and a patient 12 experiencing symptoms of fever and white spots on the inside of the mouth may visit the HCP 10 for treatment. In this example, the HCP 10 may diagnose the patient 12 as having Measles based on the symptoms and/or a positive lab test result. This diagnosis of Measles would constitute a reportable condition in the jurisdiction associated with the HCP 10 that requires the HCP 10 to report the diagnosis to a reporting entity 122 so that the reporting entity 122 can take appropriate action. As used herein, the reporting entity 122 may refer to a public health agency (PHA), such as the Centers for Disease Control and Prevention (CDC) or any combination of other government agencies/departments, responsible for managing infectious disease outbreaks to protect infectious health. For simplicity, the present disclosure will refer to the reporting entity 122 as a public health agency (PHA) 122. The PHA 122 managing infectious health may be based on the jurisdiction the HCP 10 resides. For instance, an HCP 10 licensed to treat patients 12 in the state of Michigan would be required to report reportable conditions to the PHA 122 that includes the Michigan Department of Health and Human Services (MDHHS).

In the example shown, the HCP 10 inputs patient information 14 to the HCP computing device 110 and the HCP computing device 110 provides the patient information 14 to the EHR system 150 for generating one or more types of EHR files or documents. Specifically, the HCP 10 may be a customer of a vendor that operates the EHR system 150 and the EHR system 150 is configured to generate the first document 200 associated with the first type of the C-CDA standard based on the patient information 14 input by the HCP 10 to the HCP device 110. Here, the first document 200 associated with the first type of the C-CDA standard is generated as part of standard procedure for the continued care of the patient 12 and electronic exchange of the patient information 14. The EHR system 150 may execute on the same or different remote system as the conversion manager 300. The EHR system 150 may generate a respective first document 200 (or update an existing respective first document) for each treated patient 12 after patient encounters, which may include a patient discharge, by the treating HCP 10. While human-readable via a suitable viewer displayed on a screen 114 of the HCP device 10, and accepted as a standard for secure and electronic exchange of patient information 14, documents associated with the first type of the C-CDA may not be suitable for ingestion/processing by surveillance systems/software executing on PHA computing devices 120.

The second document 250 associated with the second type of the C-CDA standard is formatted and encoded to enable a public health agency (PHA) computing device 120 associated with the PHA 122 to electronically ingest/consume specific data required in initial public health care reports so that reportable conditions can be identified and the PHA 122 can take any necessary actions. In some examples, the first document 200 associated with the first type of the C-CDA standard includes a Continuity of Care Document (CCD) and the second document 250 associated with the second type of the C-CDA standard includes an electronic initial case report (eICR) document 250. For instance, the eICR document 250 may include a standard for electronic submission of electronic initial public health case reports using HL7 Version 3 CDA, Release 2 format. Additional implementations of the present disclosure include eICR documents 250 using other versions and/or release formats currently available or specified by HL7 or other entities in the future. Thus, the eICR document 250 generated by the conversion manager 300 using the CCD 200 allows the HCP 10 to electronically communicate the specific data required by state laws/regulations for reporting reportable conditions to jurisdictional public health agencies in an interoperable, industry-standard format (e.g., C-CDA standard). As a result, the HCP 10 may continue to use the EHR system 150 to generate a standard CCD 200 based on patient information 14 (e.g., allergies, medications, problems, and laboratory results, in addition to patient header information) input by the HCP 10 via the HCP computing device 110 after patient encounters, which may include a patient discharge, and the conversion manager 300 may automatically receive the CCDs 200 and automatically generate the eICR document 250 using only relevant portions of the patient information 14 from the CCD 200 when the conversion manager 300 identifies a reportable condition in the received CCD 200. Here, the conversion manager 300 is able to leverage the CCD 200 already being generated for treated patients 10 (regardless of whether or not the patients 10 have, or are suspected to have, reportable conditions) to automatically generate and report eICR documents 250 to the proper PHAs 122, thereby fulfilling the requirements of the HCP 10 to report reportable conditions without having to undertake the burdensome and time-consuming manual process of manually filling out public health case reports and faxing/mailing the reports to the proper PHAs 122. In addition, the electronic submission of eICR documents 250 provide increased security and faster reporting of reportable conditions to the PHAs 122, while PHA computing devices 120 can electronically ingest/consume the eICR documents 250 to provide more accurate determinations of the presence of reportable conditions to manage the outbreak thereof. For simplicity, the present disclosure will refer to the first document 200 as the CCD and the second document 250 as the eICR document. In other examples, the first document 200 associated with the first type of the C-CDA standard includes a patient care document other than a CCD generated by the EHR system 150.

The conversion manager 300 executing on the remote system 140 may be operated by a third party vendor that serves as an intermediary between HCPs 10 and PHAs 122 to expediently convert CCDs 200 already being generated by certified HCPs 10 into standardized eICR documents 250 specifically formatted for electronic ingestion/consumption by PHA computing devices 120 to provide surveillance for a multitude of infectious diseases and infections. These infectious diseases and infections may include, but are not limited to, Zika virus, Measles, sexually transmitted diseases (STDs), arboviral diseases, Lyme disease, Meningitis, and Severe acute respiratory syndrome (SARS) to name a few.

In the example shown, the conversion manager 300 includes an activator 310, a parser 320, and a document generator 330. After the EHR system 150 generates the first document 200 for the patient 12 after patient encounters, which may include a patient discharge, from any inpatient, ambulatory, and/or emergency department visits to the HCP 10, the activator 310 receives the CCD 200 over the network 130 from either of the HCP computing device 110 or the EHR system 150. The first document 200 includes metadata 202 that indicates the document type. When the activator 310 determines that the metadata 202 of the received first document 200 indicates a document type associated with the first type of the C-CDA standard, and thus, is suitable for use in generating a second document 250 associated with the second type of the C-CDA standard, the activator 310 triggers the conversion manager 300 to initiate a document conversion process for generating the second document 250 by converting a portion of the patient information 14 contained in the first document 200. For example, upon receiving the first document 200, the activator 310 may analyze the metadata 202 to determine/confirm that the first document 200 is a CCD (e.g., first type of the C-CDA standard). If the first document 200 is associated with the wrong document type, the activator 310 may forgo triggering the conversion manager 300 to initiate the document conversion process and reject the first document 200. In this scenario, the conversion manager 300 may send a reply message 302 back to the HCP computing device 110 and/or the EHR system 150 indicating that the first document 200 is not a suitable document type for conversion into the second document 250 associated with the second type of the C-CDA standard. However, when the activator 310 confirms that the first document 200 is the CCD, the activator 310 provides the first document 200 to the parser 320 to begin the document conversion process.

Figure 2:
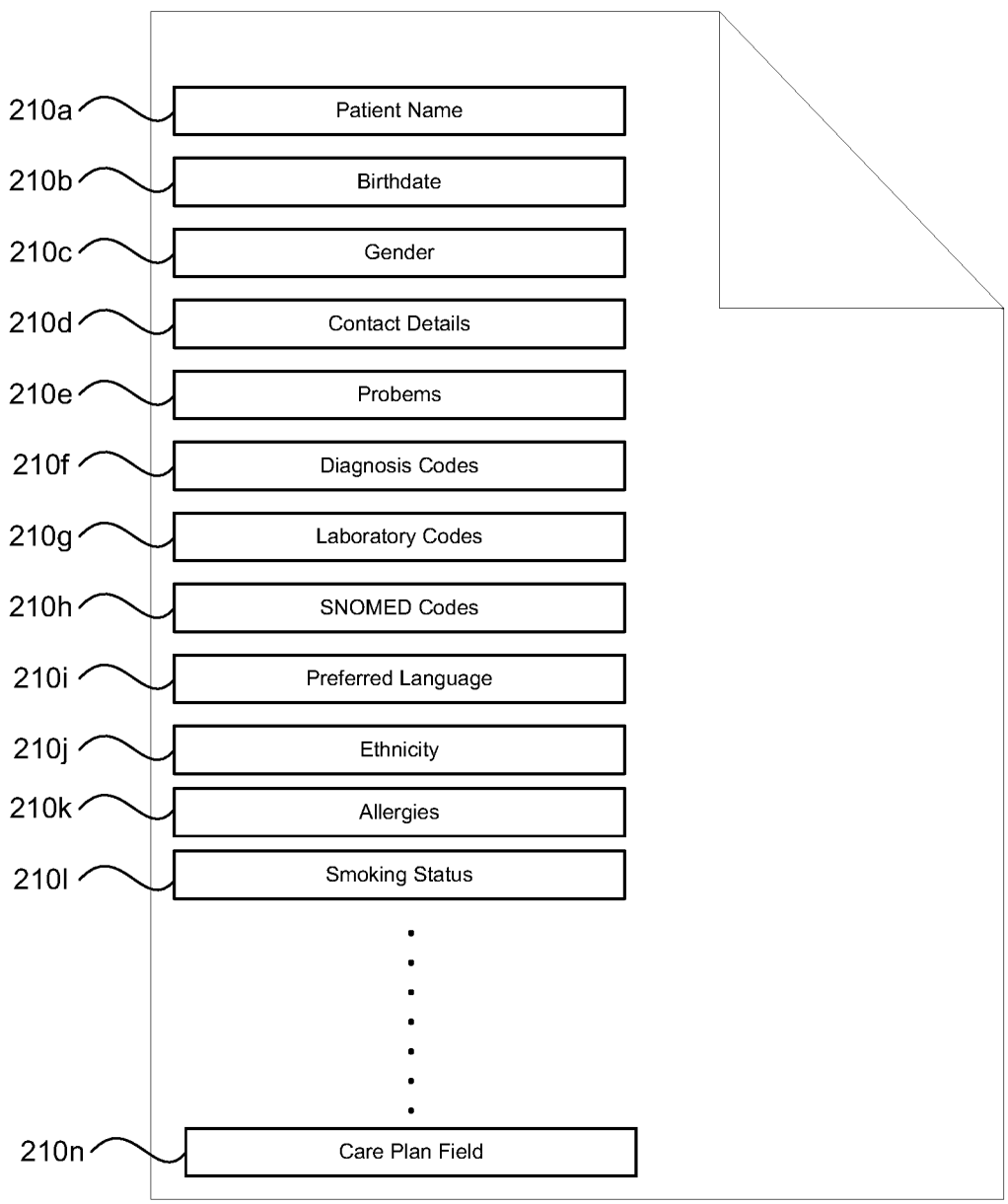
FIG. 2 is a schematic view of an example document associated with a type of a Consolidated-Clinical Document Architecture (C-CDA) standard.

The parser 320 is configured to parse the first document 200 into a plurality of patient information fields 210, 210*a*-*n* and provide the parsed first document 200 to the document generator 330. Each patient information field 210 includes respective patient information 14 associated with the treated patient 12. FIG. 2 shows an example first document 200 associated with the first type (e.g., CCD) of the C-CDA standard that includes the plurality of patient information fields 210, 210*a*-*n*. Here, the CCD 200 uses an XML-based markup standard intended to specify the encoding, structure, and semantics of a patient summary clinical document for exchange. In the example shown, the plurality of patient information fields 210, 210*a*-*n* include a patient field 210*a* that specifies a name of the patient 12, a birthdate field 210*b* that provides the patient's 12 date of birth, a gender field 210*c* that provides the patient's gender, a contact details field 210*d* that provides contact information (address/phone number/email address) for the patient 12, one or more problems fields 210*e* that indicate problems/conditions the patient 12 has and/or has been treated for, diagnosis codes field 210*f* that provide diagnosis codes of the patient 12 input by HCPs 10 that indicate a diagnosis of the patient 12, laboratory codes field 210*g* including a list of laboratory codes (e.g., Laboratory Observation Identifiers Names and Codes (LOINC)) that provide values/results of specific laboratory tests performed on the patient 12, Systematized Nomenclature of Medicate (SNOMED) codes field 210*h* providing SNOMED codes associated with the patient 12, a preferred language field 210i indicating a language the patient 12 prefers to use to communicate, an ethnicity field 210j indicating an ethnicity of the patient 12, one or more allergies fields 210k indicating allergies of the patient, a smoking status field 210l indicating whether or not the patient 12 smokes/uses tobacco, and a care plan field 210n indicating treatment goals of the patient 12. The patient information fields 210 of the CCD 200 are non-exhaustive and the CCD 200 includes many more fields that are important for documenting for the continued treatment of the patient 12. While the CCD 200 includes a multitude of patient information fields 210 to convey/document patient information 14 with a high degree of granularity for continued care of the patient 12, the eICR document 250 electronically processed by the PHA computing device 120 requires far fewer patient information fields 260 (FIG. 1) that convey only the necessary patient information 14 needed by the proper PHA 122 to manage infectious diseases corresponding to the reportable conditions. For instance, PHA 122 may only require the patient's 12 name, demographic information, contact details, diagnosis codes, laboratory codes, and/or SNOMED codes in order to effectively manage/prevent the outbreak of infectious diseases.

Referring back to FIG. 1, in some implementations, the document generator 330 is configured to receive the parsed first document 100 from the parser 200 and determine whether any of the plurality of patient information fields 210 in the parsed first document 200 include a reportable condition. Reportable conditions may be specified by one or more PHAs 122 in the controlling jurisdiction of the HCP (e.g., the jurisdiction the HCP resides in or the jurisdiction associated with locations where the patient was treated) and/or the controlling jurisdiction where the patient 10 currently resides or plans to travel to. Accordingly, reportable conditions may be jurisdiction-dependent such that a condition may be required by law to be reported to the proper PHA 122 in one jurisdiction but not in another jurisdiction. In some implementations, PHAs 122 in each of a multitude of jurisdictions (i.e., different countries, states, territories, counties, cities/towns) each store, via a PHA computing device 120, a respective list of reportable conditions 350 in a reportable condition datastore 340. The reportable condition datastore 340 may reside on memory hardware 520 (FIG. 5) (e.g., storage resources 146) of the remote system 140 or may be located at some other remote storage location in communication with the conversion manager 300. In these implementations, each list of reportable conditions 350 includes reportable conditions specified by the controlling PHA 120 of the corresponding jurisdiction. The list of reportable conditions 350 may identify specific diseases/infections, diagnosis codes, laboratory codes, SNOMED codes, and/or other codes indicative of a 'reportable condition' that an HCP 10 under the supervision of the controlling PHA is required by law to report to the PHA 120. For instance, the disease Gonorrhea may in and of itself be a reportable condition, however, Gonorrhea may also be identified by a multitude of different diagnosis codes, laboratory codes, and/or SNOMED codes. As such, the list of reportable conditions 350 may specify multiple diagnosis codes, laboratory codes, and/or SNOMED codes that each constitute a respective reportable condition associated with Gonorrhea and must be reported to the proper PHA 122 when identified in any of the patient information fields 210 of the parsed first document 200. The PHAs 122 may input their respective lists of reportable conditions 350 to the reportable condition datastore 340 directly, or the PHAs 122 may provide the lists of reportable conditions 350 to the conversion manager 300 and the conversion manager 300 may store the lists in the datastore 340. Moreover, the conversion manager 300 could harvest lists of reportable conditions 350 associated with PHAs 122 using various techniques and store the harvested lists in the datastore 340. In some configurations, the conversion manager 300 tags each list of reportable condition with an identifier and/or jurisdiction of the respective PHA 122 so that the appropriate list of reportable conditions 350 can be mapped to the CCD 200. In additional examples, the document generator 330 obtains the list of reportable conditions 350 by querying the PHA 122 directly or by accessing a website or other source associated with the controlling PHA 122 that provides access to the list of reportable conditions 350.

In some examples, the document generator 330 obtains the list of reportable conditions 350 from the reportable condition datastore 340 to determine if any of the patient information fields 210 include one of the reportable conditions in the obtained list of reportable conditions 350. In some examples, the document generator 330 may analyze the parsed first document 200 to identify a location of the controlling jurisdiction that specifies reportable conditions, and query the reportable condition datastore 340 using the identified location to obtain the list of reportable conditions 350 specified by the proper PHA 122 of the controlling jurisdiction. Here, each list of reportable conditions 350 stored in the datastore 340 may include a respective geographical location tag (or other indicator that correlates to the controlling jurisdiction) indicating the geographical area associated with the respective PHA 120 of the controlling jurisdiction. In additional examples, the metadata 202 of the first document may include the location of the controlling jurisdiction based on where the HCP 10 is licensed to practice and/or where the patient 10 treated. The document generator 330 may determine that at least one patient information field 210 includes the reportable condition when at least one of a diagnoses code field 210f includes a diagnosis code indicative of the reportable condition, a laboratory codes filed 210g includes a laboratory code indicative of the reportable condition, or a SNOMED codes field 210h includes a SNOMED code indicative of the reportable condition.

In some implementations, the document generator 330 only generates the second document 250 associated with the second type of the C-CDA standard when at least one reportable condition is identified in the parsed first document 200. Accordingly, if the document generator 330 determines that none of the plurality of patient information fields 210 in the parsed first document 200 include a reportable condition, the document generator 330 will cease/terminate the document conversion process and forgo generating the second document 250 (e.g., the eICR document 250). In this scenario, since the CCD 200 does not indicate the presence of a reportable condition, there is no need for the conversion manager 300 to generate an eICR document 250 for reporting to a PHA 122. Optionally, the conversion manager 300 may send a response message 302 back to the HCP computing device 110 and/or the EHR system 150 indicating that an eICR document 250 will not be generated because a reportable condition was not identified in the received CCD. However, since the conversion manager 300 provides an automated service that automatically receives CCDs generated by the EHR system 150 after patient encounters, which may include a patient discharge, the conversion manager 300 may be configured to simply cease/terminate the document conversion process in the absence of a reportable condition without ever sending the response message 302.

In the example shown, when the document generator 300 determines that at least one patient information field 210 in the parsed first document 200 includes the reportable condition, the document generator 300 responsively generates, using the first document 200, the second document 250 associated with the second type of the C-CDA standard and including the reportable condition. For instance, in response to identifying the reportable condition in a patient information field 210 of the parsed CCD 200, the document generator 300 may generate the eICR document 250 using only a portion of the patient information 14 from the CCD 200 that is required for inclusion eICR documents, e.g., as specified by the standard for electronic submission of electronic initial public health case reports using HL7 Version 3 CDA, Release 2 format. Thereafter, the conversion manager 300 may transmit the generated second document 250 (e.g., eICR document) to the PHA computing device 120 associated with the proper PHA 122. The second document 250 is generated by populating required fields 260A (FIG. 3C) specified by the second type of the C-CDA standard with only the required patient information 14 converted from the CCD 200. The required patient information 14 includes only patient information 14 needed by the PHA 122 to identify reportable conditions and manage outbreak of infectious diseases indicated by the reportable conditions. Generally, the required patient information 14 populated into the required fields 260A (FIG. 3C) includes the reportable conditions (i.e., diagnosis codes, laboratory codes, SNOMED codes, etc.), the patient's name, and the patient's contact details (e.g., residence address, phone number, email, etc.). Thus, a vast majority of the other patient information 14 included in the CCD 200 is identified as unnecessary patient information 14 to be omitted from eICR documents 250.

In some implementations, the conversion manager 300 further applies data cleansing on the generated second document 200 to detect and correct/remove corrupt, inaccurate, incomplete, or irrelevant data from the second document 200. For instance, the data cleansing may ensure that grammar conforms to a specified standard programming language, e.g., JavaScript, to ensure that the PHA computing device 120 is able to ingest and process the second document 200 containing the reportable condition. Additionally, the conversion manager 300 may apply a style sheet to the second document and/or add comments into code for easier human-readable presentation on a display of the PHA computing device 120.

Figure 3A:
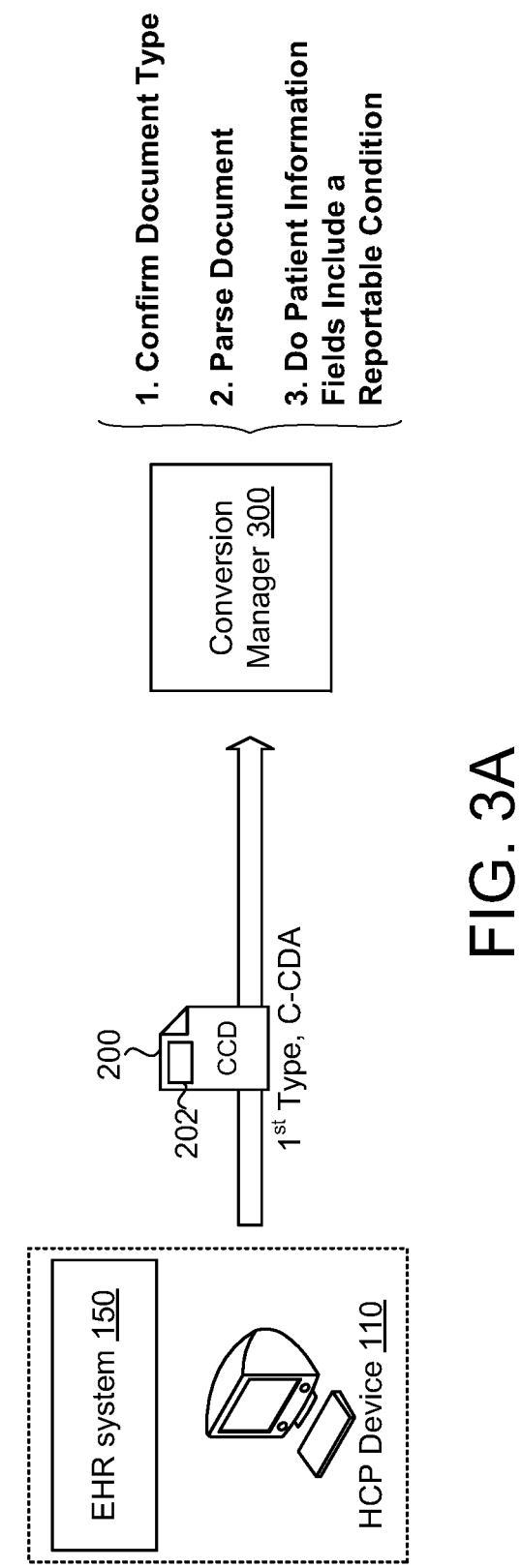
FIGS. 3A-3C are schematic views of exemplary operations performed by a conversion manager of the electronic case reporting system for generating documents.
Figure 3B:
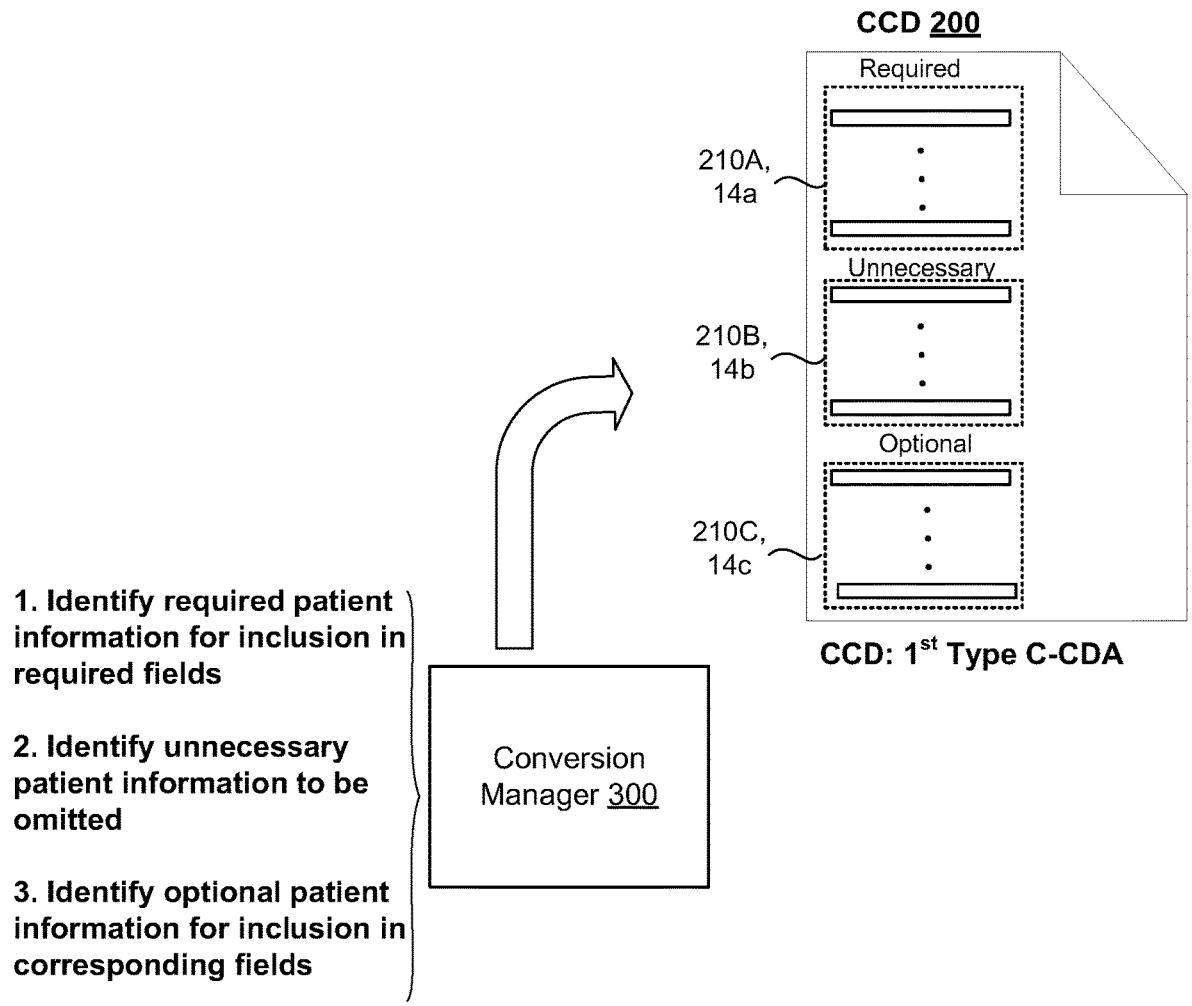
Figure 3C:
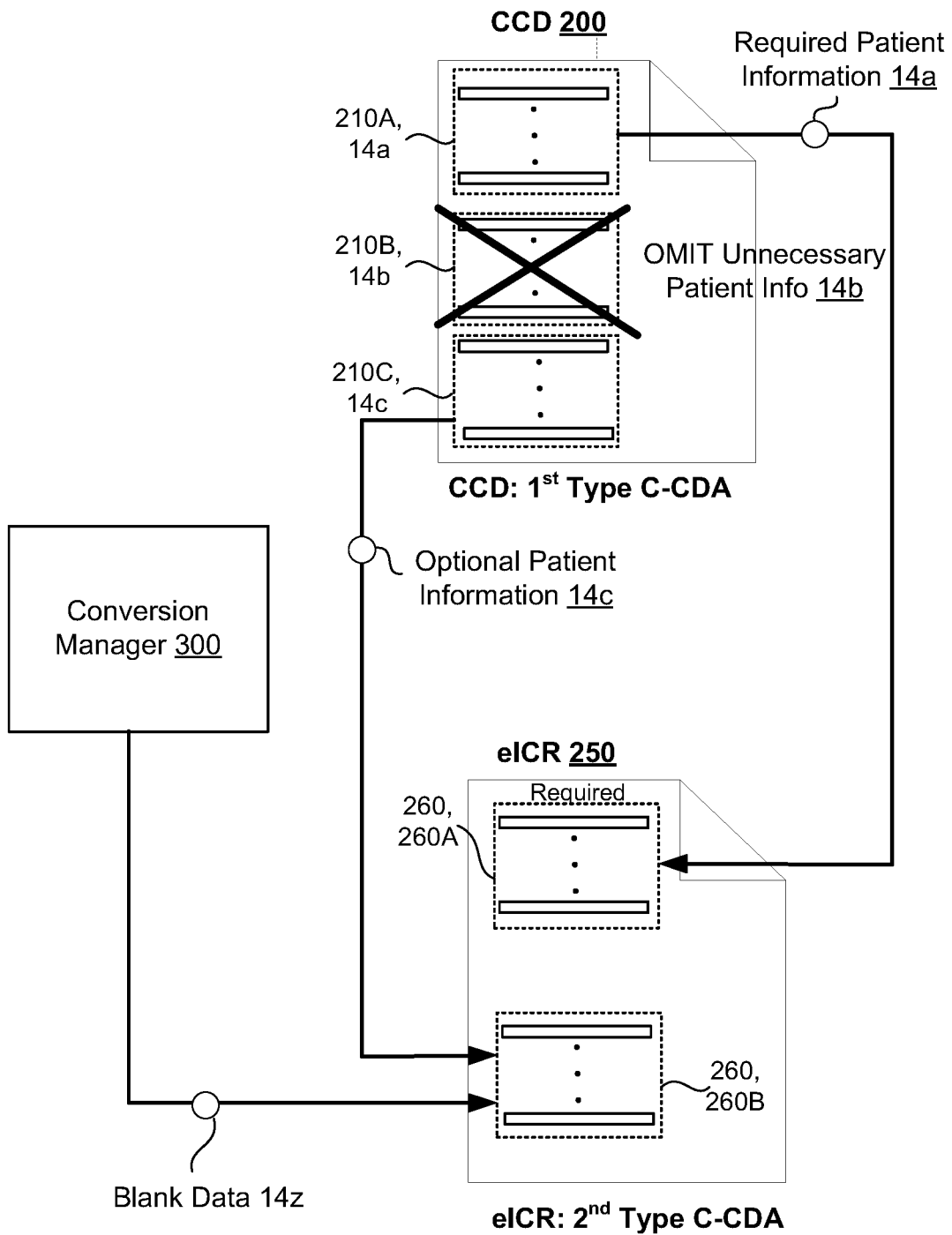

FIGS. 3A-3C provide schematic views of the conversion manager 300 receiving a first document 200 (e.g., CCD) associated with a first type of the C-CDA standard and using the first document 200 to generate a second document 250 (e.g., eICR) associated with a second type of the C-CDA standard when the first document 200 includes a reportable condition. Referring to FIG. 3A, the conversion manager 300 receives the first document 200 including patient information 14 associated with a patient 12 treated by a HCP 10. The conversion manager 300 may receive the first document 200 from an HCP computing device 110 associated with the treating HCP 10 or from an EHR system 150 that generated the first document 200 based on the patient information 14 input to the HCP computing device 110 by the HCP 10. The conversion manager 300 (e.g., using the activator 310) must first confirm that the received first document 200 is associated with the first type of the C-CDA standard. Here, the conversion manager 300 may analyze metadata 202 indicating the document type and confirm that the document type matches the first type of the C-CDA standard. In the example shown, the conversion manager 300 is simply confirming that the first document includes a document type corresponding to a Continuity of Care Document (CCD). If the conversion manager 300 (e.g., the activator 310) determines that the document type associated with the received first document 100 does not include the first type (e.g., CCD) of the C-CDA standard, then the conversion manager 300 will reject the first document 200. The conversion manager 300 may optionally send a response message 302 to the EHR system 150 or HCP computing device 110 indicating that the received first document 200 is an improper document type for generating documents (eICR documents) associated with the second type of the C-CDA standard.

With continued reference to FIG. 3A, when the conversion manager 300 confirms that the received first document 100 is associated with the first type of the C-CDA standard (i.e., the first document 200 is a CCD), the conversion manager 300 (e.g., via the parser 320) scans the entire first document 200 and parses the first document 200 into a plurality of patient information fields 210 each conveying a respective portion of the patient information 14 associated with the treated patient 12. Example patient information fields 210 parsed from an example C-CDA document 200 is described above with reference to FIG. 2. Thereafter, the conversion manager 300 (e.g., via the document generator 330) determines whether any of the plurality of patient information fields 210 in the parsed first document 200 include a reportable condition. For instance, the conversion manager 300 may obtain a list of reportable conditions 350 from a reportable condition data store 340 and determine that at least one patient information field 210 includes one of the reportable conditions in the list of reportable conditions 350 obtained from the datastore 340. As discussed above, the obtained list of reportable conditions 350 may be specified by one or more PHAs 122 in the controlling jurisdiction of the HCP 10 or patient 12. Accordingly, the datastore 340 may include a plurality of lists of reportable conditions 350 each associated with a respective jurisdiction and including reportable conditions 350 specified by the PHA 122 of the respective jurisdiction. Thus, the conversion manager 300 may extract a geographical location identifier (e.g., address of clinic where patient 12 was treated by HCP 10) from the parsed first document 200 (or from the metadata 202) and use the geographic location identifier to obtain the appropriate list of reportable conditions 350.

When none of the patient information fields 210 include a reportable condition, the conversion manager 300 may end a document conversion process and will not generate the second document 250 (e.g., eICR) associated with the second type of the C-CDA standard. The conversion manager 300 may optionally send a response message 302 to the EHR system 150 or HCP computing device 110 indicating that the received first document 200 does not include a reportable condition.

On the other hand, when the conversion manager 300 determines that at least one patient information field 210 in the parsed first document 200 includes the reportable condition, the conversion manager 300 continues the document conversion process to initiate generating the second document 250 associated with the second type of the C-CDA standard. In this scenario, the conversion manager 300 may send a response message 302 to the EHR system 150 or HCP computing device 110 indicative of a reportability response indicating that a reportable condition was identified in the first document 200 and the second document 200 (e.g., eICR) document will be generated and transmitted to the proper PHA 122 for reporting the reportable condition. In some examples, the conversion manager 300 waits until the eICR document is successfully generated and successfully transmitted to the proper PHA 122 before sending the reportability response 302.

FIG. 3B shows operations performed by the conversion manager 300 during generation of the second document 250 associated with the second type of the C-CDA standard. The second type of the C-CDA standard, e.g., the standards for generating eICR documents, may specify required patient information 14, 14*a* required for inclusion in documents 250 (e.g., eICR) associated with the C-CDA standard. Here, the required patient information 14*a* corresponds to only the relevant information/data necessary for reporting a reportable condition to the proper PHA so that the PHA 122 can effectively manage outbreaks of infectious diseases. Based on this specification, the conversion manager 300 is configured to identify, from a first portion 210A of the plurality of patient information fields 210 in the parsed first document (e.g., CCD) 200, the required patient information 14*a*. In some examples, the required patient information 14*a* includes the name of the treated patient 12, reportable conditions (e.g., diagnostic codes, laboratory codes, SNOMED codes), and how to reach the patient (e.g., contact information). Additionally, the second type of the C-CDA standard may specify unnecessary patient information 14, 14*b* to be omitted from documents (e.g. eICR) associated with the second type of the C-CDA standard. Here, the conversion manager 300 may further identify, from a second portion 210B of the plurality of patient information fields 210 in the parsed first document (e.g., CCD) 200, the unnecessary patient information 14*b*. In some examples, the second portion 210B of the plurality of patient information fields 210 including unnecessary patient information 14*b* includes a greater number of patient information fields than the first portion 210A of the plurality of patient information fields 210 including the required patient information 14*a*.

In some scenarios, when parsed first document 200 is missing any portion of the required patient information 14*a*, the conversion manager 300 ceases generating the second document 250 since the specifications of the second document 250 require the required patient information 14*a* that is missing in the first document 200. Thus, the requirement that all required patient information 14*a* exists in the parsed first document 200 is a condition that must be satisfied in order for the conversion manager 300 to generate the second document 250. In these scenarios when the condition is not satisfied due to the conversion manager failing to identify any portion of the required patient information 14*a* in the parsed first document 200, the conversion manager 300 may send a response message 302 (i.e., a failed conversion message) to the HCP computing device 110 or the EHR system 150 indicating that the received first document 200 is missing required patient information 14*a* and that an updated first document 200 with the required patient information 14*a* that was previously missing needs to be resubmitted to the conversion manager 300. For instance, the response message 302 when received by the HCP computing device 110 or the EHR system 150 may cause the HCP computing device 110 or the EHR system 150 to display on a screen (e.g., display 114) details of the specific required patient information 14*a* that was missing and needed by the conversion manager 300 to generate the second document 250. In some scenarios, rather than requiring generation of an updated first document 200, the HCP computing device 110 or the EHR system 150 transmits the required patient information 14*a* identified in the response message 302 as being missing from the previously transmitted first document and the conversion manager 300 modifies the first document 200 to now include required patient information 14*a* so that the second document 250 can be generated. In these scenarios, the HCP 10 may input the required patient information 14*a* identified in the response message 302 to the computing device 110 or the EHR system 150 may automatically obtain the required patient information 14*a* without requiring any input from the HCP 10 or other user. Optionally, the conversion manager 300 may determine that all the required patient information 14*a* is available upon receiving the previously missing required patient information 14*a* and generate the second document 250 using the required patient information 14*a* without modifying the first document 200.

In additional implementations, the second type of the C-CDA standard, e.g., the standards for generating eICR documents, further specifies one or more fields 260B (FIG. 3C) to be created in documents (e.g., eICR) associated with the second type of the C-CDA standard. In these implementations, for each field 260B, the conversion manager 300 determines, from a third portion 210C of the plurality of patient information fields 210 in the parsed first document 200, whether corresponding optional patient information 14*c* exists for inclusion in the corresponding field. As used herein, fields 260B" refer to optional fields from the first type of the C-CDA standard that must be created in documents associated with the second type of the C-CDA standard (e.g., eICR) that are associated with information that is necessary to effectively report reportable conditions to PHAs 122 for public health awareness. That is to say, when the conversion manager 300 determines that any optional patient information 14*c* corresponding to one or more of the fields 260B to be created in the second document 250 do not exist in the parsed first document (e.g., CCD) 200, the conversion manager 300 will still proceed to generate the second document 250 by creating the corresponding one or more of the fields 260B with blank information 14*z* (FIG. 3C) so that the second document 250 passes verification at the receiving PHA computing device 120, e.g., a verifier at the PHA computing device 120 verifies that the second document 250 meets the standards specified for documents (eICR documents) associated with the second type of the C-CDA standard.

Referring to FIG. 3C, when the conversion manager 300 satisfies the condition by identifying all of the required patient information 14*a* from the parsed first document 250, the conversion manager 300 is configured to generate the second document 250 by populating the required fields 260A with the corresponding required patient information 14*a* identified from the first portion 210A of the plurality of patient information fields 210 in the parsed first document 200. Here, the population of the required fields 260A includes techniques of extracting the required patient information 14*a* from the first document 200 and converting the required patient information 14*a* into an appropriate format/language required for inclusion in the corresponding required field 260A of the second document 250. At the same time, the conversion manager 300 omits populating the second document 250 with any of the unnecessary information 14*b* identified from the second portion 210B of the plurality of patient information fields 210 in the parsed first document 200.

Moreover, the conversion manager 300 creates each field 260B as specified by the second type of the C-CDA standard for inclusion in the second document (e.g., eICR). Here, for each field 260 in which the conversion manager 300 determines corresponding optional patient information 14c exists in the parsed first document 200 (e.g., from the third portion 210C of the plurality of patient information fields 210), the conversion manager populates the corresponding field 260B with the corresponding optional patient information 14c converted from the parsed first document 200. On the other hand, for each field 260B in which the conversion manager 300 determines the corresponding optional patient information 14c does not exist in the parsed first document 200, the conversion manager populates the corresponding field 260B with blank data 14z so that the generated second document (eICR) 250 associated with the second type of the C-CDA standard passes verification when received by the proper PHA device 120.

Figure 4:
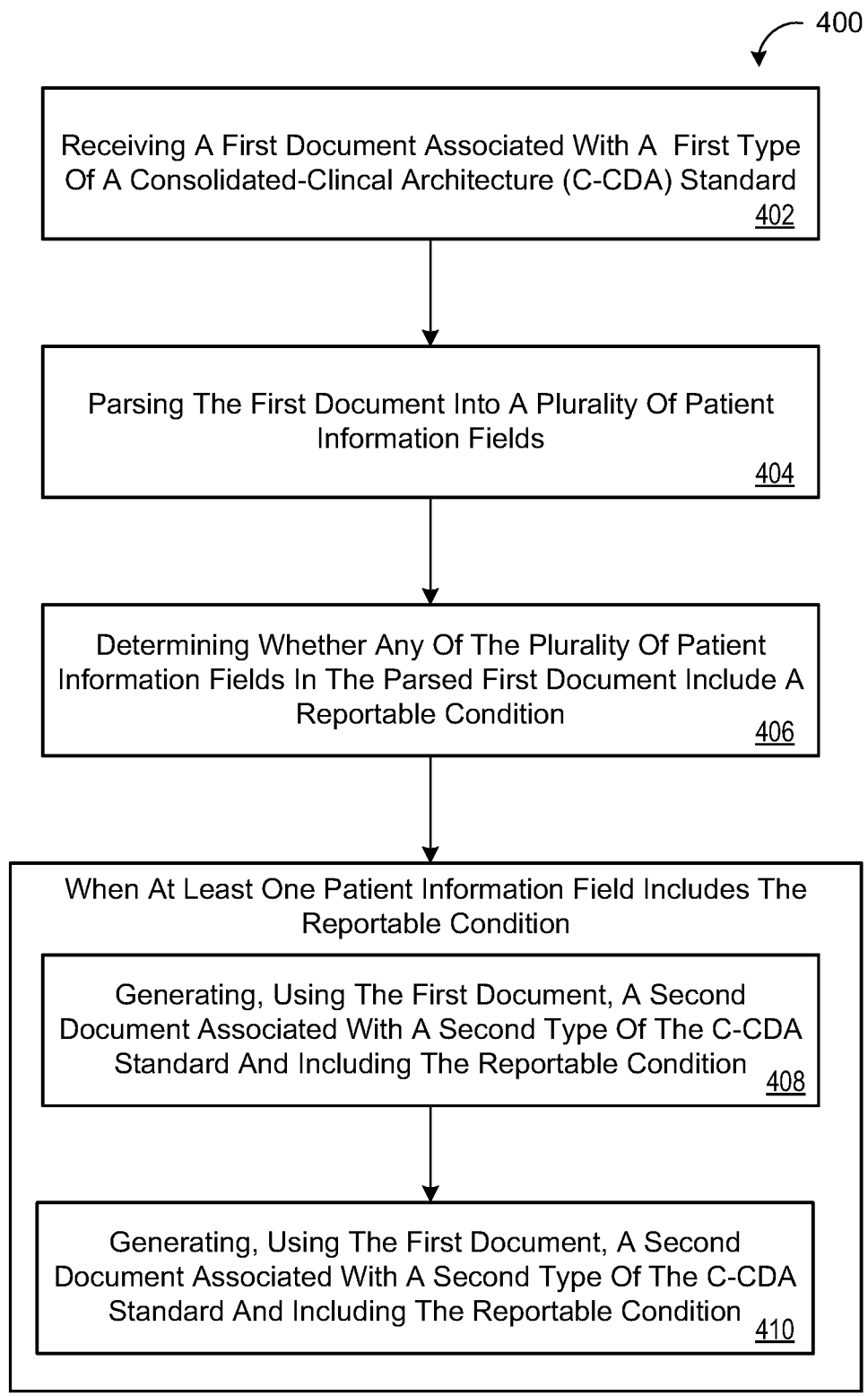
FIG. 4 is a flowchart of an example arrangement of operations for a method of electronically reporting a reportable condition.

FIG. 4 provides a flowchart for an exemplary arrangement of operations for a method 400 of electronically reporting a reportable condition to a public health agency (PHA) 122. The method 400 may execute on data processing hardware 510 (FIG. 5) residing on the remote system 140 (e.g., computing resources 144) by executing instructions stored on memory hardware 520 (FIG. 5) (e.g., storage resources 146) in communication with the data processing hardware 510. Here, the data processing hardware 510 executes the conversion manager 300.

At operation 402, the method 400 includes receiving, at the data processing hardware 510, a first document 200 associated with a first type of a C-CDA standard. The first document includes patient information 14 associated with a patient 12 treated by a healthcare professional (HCP) 10. In some examples, the first document 200 includes a standard Continuity of Care Document (CCD) generated by an electronic health record (EHR) system 150 after patient encounters, which may include a patient discharge, based on patient information 14 input by the treating HCP 10. In other examples, the first document 200 includes a patient care document generated by the EHR system 150. The patient care document can be any type of patient summary document in existence, or developed in the future, that contains patient care information. At operation 404, the method 400 includes parsing, by the data processing hardware 510, the first document 200 into a plurality of patient information fields 210, 210a-n.

At operation 406, the method 400 includes determining, by the data processing hardware 510, whether any of the plurality of patient information fields 210 in the parsed first document 200 include a reportable condition. Here, data processing hardware 510 may obtain a list of reportable conditions 350 from a reportable condition datastore 340, wherein the list of reportable conditions 350 are specified by a controlling PHA 120. Here, the list of reportable conditions 350 may be directly input to the datastore 340 by a PHA computing device 120 associated with the PHA 120 or the PHA computing device 120 may provide the list to the conversion manager 300 and the conversion manager 300 may store the list in the datastore 340. At least one patient information field 210 is determined to include a reportable condition when the at least one patient information field includes one of the reportable conditions in the obtained list of reportable conditions 350. Here, the PHA 120 is based on a controlling jurisdiction associated with the HCP 10 and/or treated patient 12. Accordingly, many lists of reportable conditions 350 may exist where each list is associated with a corresponding jurisdiction and includes respective reportable conditions specified by the PHA 120 of the corresponding jurisdiction. A patient information field 210 includes the reportable condition when the patient information field 210 includes a diagnosis code indicative of the reportable condition, a laboratory code indicative of the reportable condition, or a SNOMED code indicative of the reportable condition.

At operation 408, when at least one patient information field 210 of the plurality of patient information fields includes the reportable condition, the method 400 includes generating, by the data processing hardware 510, using the first document 200, a second document 250 associated with a second type of the C-CDA standard. The second document 250 includes the reportable condition. The second type of the C-CDA standard is different than the first type of the C-CDA standard. In some examples, the second document 250 includes an electronic initial case report (eICR) document using HL7 Version 3 CDA, Release 2 format.

In some implementations, the data processing hardware 510 only generates the second document when the condition of identifying all required patient information 14a in the parsed first document 200 that is required for inclusion in the second document 200 is satisfied. When the condition is not satisfied, the data processing hardware 510 may send a response message 302 (i.e., a failed conversion message) to the HCP informing the HCP that the second document could not be generated since some or all required patient information 14a is missing from the first document 200. The message 302 may indicate details of the missing required patient information 14a so that the HCP can provide the information 14a to satisfy the condition.

At operation 410, the method 400 also includes transmitting, by the data processing hardware 510, the second document 250 to a PHA computing device 120 associated with a PHA 120. The PHA computing device 120 is configured to process the second document 250 to extract the reportable condition from the second document 250. Operation 410 is optional such that the second document 250 will be generated, but not sent to the PHA computing device 120 in scenarios when trigger codes are found in non-required sections/fields (e.g., history of past illness section) of documents 250 (e.g., eICR) associated with the C-CDA standard. In some examples, the PHA computing device 120 first verifies that the second document 250 includes all required fields 260A populated with corresponding required patient information 14a (e.g., patient name, reportable condition, patient contact details, patient demographics) and all fields 260B have been created. As discussed above, fields 260B populated with blank data to allow the second document 250 to pass verification when corresponding optional patient information 14b does not exist in the first document 200.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

Figure 5:
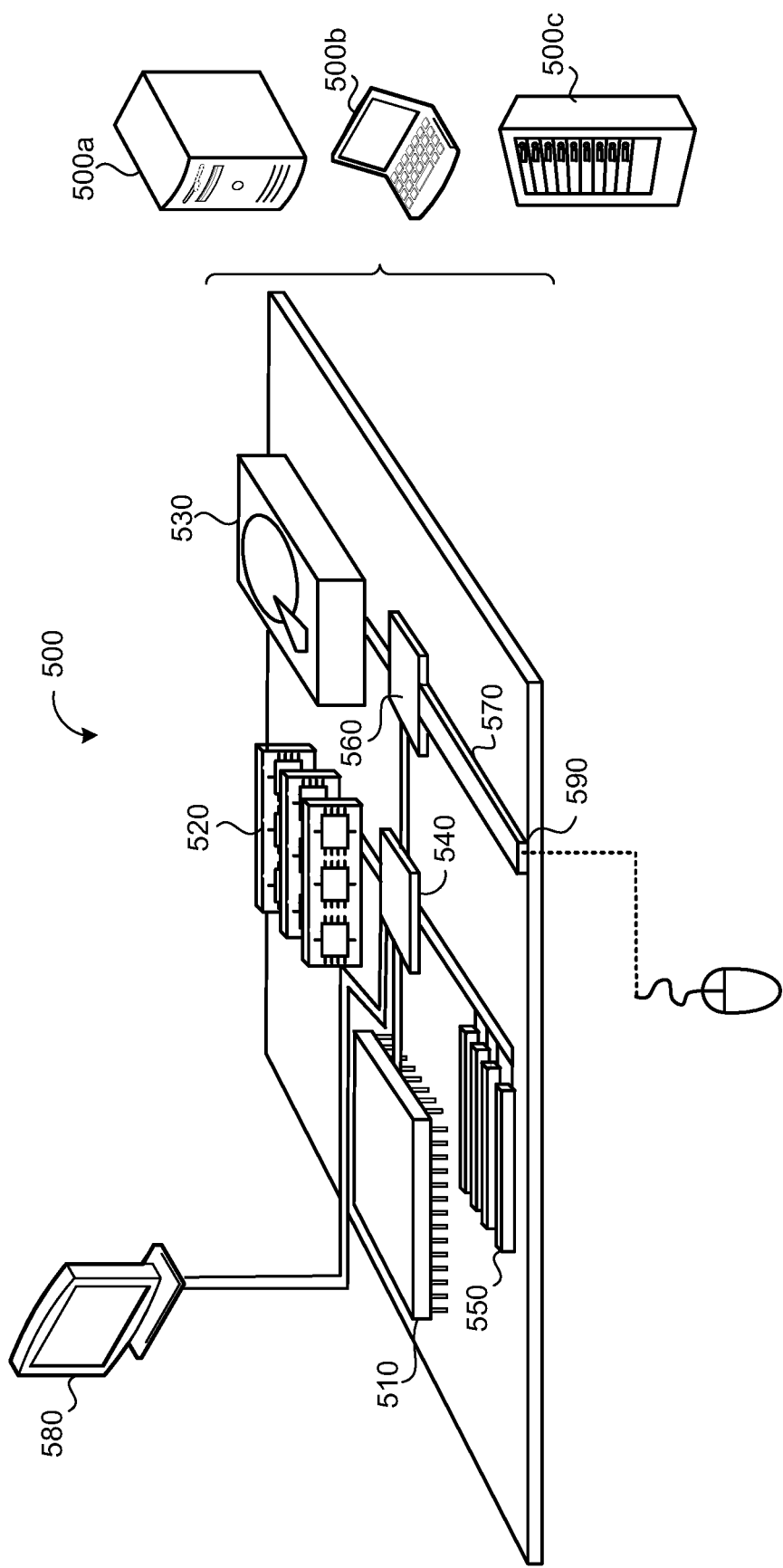
FIG. 5 is a schematic view of an example computing device that may be used to implement the systems and methods described herein.

FIG. 5 is schematic view of an example computing device 500 that may be used to implement the systems and methods described in this document. The computing device 500 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 500 includes a processor 510 (e.g., data processing hardware executing the conversion manager 300), memory 520, a storage device 530, a high-speed interface/controller 540 connecting to the memory 520 and high-speed expansion ports 550, and a low speed interface/controller 560 connecting to a low speed bus 570 and a storage device 530. Each of the components 510, 520, 530, 540, 550, and 560, are interconnected using various busses, and may be mounted on a common motherboard or in other manners as appropriate. The processor 510 can process instructions for execution within the computing device 500, including instructions stored in the memory 520 or on the storage device 530 to display graphical information for a graphical user interface (GUI) on an external input/output device, such as display 580 coupled to high speed interface 540. In other implementations, multiple processors and/or multiple buses may be used, as appropriate, along with multiple memories and types of memory. Also, multiple computing devices 500 may be connected, with each device providing portions of the necessary operations (e.g., as a server bank, a group of blade servers, or a multi-processor system).

The memory 520 (e.g., memory hardware) stores information non-transitorily within the computing device 500. The memory 520 may be a computer-readable medium, a volatile memory unit(s), or non-volatile memory unit(s). The non-transitory memory 520 may be physical devices used to store programs (e.g., sequences of instructions) or data (e.g., program state information) on a temporary or permanent basis for use by the computing device 500. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 530 is capable of providing mass storage for the computing device 500. In some implementations, the storage device 530 is a computer-readable medium. In various different implementations, the storage device 530 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 520, the storage device 530, or memory on processor 510.

The high speed controller 540 manages bandwidth-intensive operations for the computing device 500, while the low speed controller 560 manages lower bandwidth-intensive operations. Such allocation of duties is exemplary only. In some implementations, the high-speed controller 540 is coupled to the memory 520, the display 580 (e.g., through a graphics processor or accelerator), and to the high-speed expansion ports 550, which may accept various expansion cards (not shown). In some implementations, the low-speed controller 560 is coupled to the storage device 530 and a low-speed expansion port 590. The low-speed expansion port 590, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 500a or multiple times in a group of such servers 500a, as a laptop computer 500b, or as part of a rack server system 500c.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A method of electronically reporting a reportable condition, the method comprising:
   receiving, at data processing hardware, a first document comprising patient information associated with a patient treated by a healthcare provider (HCP);
   determining, based on metadata of the first document, whether the first document is associated with a first type of a Consolidated Clinical Document Architecture (C-CDA) standard;
   when the first document is associated with the first type of the C-CDA standard, initiating a document conversion process comprising:
      scanning, by the data processing hardware, the first document, the scanned first document comprising a plurality of patient information fields;
      determining, by the data processing hardware, whether any of the plurality of patient information fields in the scanned first document comprise a reportable condition; and
      in response to determining that at least one patient information field of the plurality of patient information fields comprises the reportable condition, generating, by the data processing hardware, using the first document, a second document associated with a second type of the C-CDA standard and comprising the reportable condition by:
         identifying, from a first portion of the plurality of patient information fields in the scanned first document, required patient information, the required patient information required for inclusion in documents associated with the second type of the C-CDA standard;
         identifying, from a second portion of the plurality of patient information fields in the scanned first document, unnecessary patient information, the unnecessary patient information specified by the second type of the C-CDA to be omitted from documents associated with the second type of the C-CDA standard; and
         generating the second document by populating required fields specified by the second type of the C-CDA standard with the required patient information identified from the first portion of the plurality of patient information fields in the scanned first document and omitting populating the second document with the unnecessary patient information identified from the second portion of the plurality of patient information fields in the scanned first document; and
   when the first document is not associated with the first type of the C-CDA standard, rejecting the first document,
   wherein the second type of the C-CDA standard is different than the first type of the C-CDA standard, and wherein the generated second document associated with the second type of the C-CDA standard is encoded and specifically formatted for electronic ingestion by a public health agency (PHA) computing device associated with a PHA to identify the reportable condition in the second document.

2. The method of claim 1, further comprising, after generating the second document, automatically transmitting, by the data processing hardware, the second document electronically to the PHA computing device associated with the PHA, the PHA computing device configured to process the second document to extract the reportable condition from the second document.

3. The method of claim 1, wherein the first type of the C-CDA standard comprises a Continuity of Care Document (CCD) generated by an electronic health record (EHR) system, the EHR system configured to:
   receive the patient information from a HCP device associated with the patient, the patient information input to the HCP device by the HCP; and
   generate the CCD based on the received patient information.

4. The method of claim 1, wherein the first type of the C-CDA standard comprises a patient care document generated by an electronic health record (EHR) system, the EHR system configured to:
   receive the patient information from a HCP device associated with the patient, the patient information input to the HCP device by the HCP; and
   generate the patient care document based on the received patient information.

5. The method of claim 1, wherein the second type of the C-CDA standard comprises an Electronic Initial Case Report (eICR).

6. The method of claim 1, further comprising:
   determining, by the data processing hardware, that the second type of the C-CDA standard specifies one or more optional fields from the first type of the C-CDA standard to be created in documents associated with the second type of the C-CDA standard; and for each optional field:
based on metadata of the first document, determining, by the data processing hardware, from a third portion of the plurality of patient information fields in the scanned first document, whether corresponding optional patient information exists for inclusion in the corresponding field; and one of
when the corresponding optional patient information exists, populating, by the data processing hardware, the corresponding field specified by the second type of the C-CDA standard with the corresponding optional patient information; or
when the corresponding optional patient information does not exist, populating, by the data processing hardware, the corresponding field specified by the second type of the C-CDA standard with blank data.

7. The method of claim 1, wherein determining whether any of the plurality of patient information fields in the scanned first document comprise the reportable condition comprises:
obtaining a list of reportable conditions from a reportable condition datastore in communication with the data processing hardware, the list of reportable conditions specified by the PHA; and
determining that the at least one patient information field of the plurality of patient information fields comprises one of the reportable conditions in the list of reportable conditions obtained from the reportable condition datastore.

8. The method of claim 1, wherein the at least one patient information field of the plurality of patient information fields comprises the reportable condition when the at least one patient information field comprises a diagnoses code indicative of the reportable condition.

9. The method of claim 1, wherein the at least one patient information field of the plurality of patient information fields comprises the reportable condition when the at least one patient information field comprises a laboratory code indicative of the reportable condition.

10. The method of claim 9, wherein the laboratory code indicative of the reportable condition comprises a Laboratory Observation Identifiers Names and Codes (LOINC) code.

11. The method of claim 1, wherein the at least one patient information field of the plurality of patient information fields comprises the reportable condition when the at least one patient information field comprises a Systematized Nomenclature of Medicate (SNOMED) code indicative of the reportable condition.

12. The method of claim 1, further comprising, prior to generating the second document associated with the second type of the C-CDA standard:
determining, by the data processing hardware, whether any of the plurality of patient information fields in the scanned first document are missing corresponding required patient information required for generating documents associated with the second type of the C-CDA standard; and
when one or more of the plurality of patient information fields in the scanned first document are missing the corresponding required patient information, ceasing, by the data processing hardware, the generating of the second document associated with the second type of the C-CDA standard.

13. The method of claim 1, further comprising, when none of the plurality of patient information fields in the scanned first document comprise the reportable condition, forgoing, by the data processing hardware, the generating of the second document associated with the second type of the C-CDA standard using the first document.

14. A system comprising:
data processing hardware; and
memory hardware in communication with the data processing hardware and storing instructions that when executed on the data processing hardware cause the data processing hardware to perform operations comprising:
receiving a first document comprising patient information associated with a patient treated by a healthcare provider (HCP);
determining, based on metadata of the first document, whether the first document is associated with a first type of a Consolidated Clinical Document Architecture (C-CDA) standard;
when the first document is associated with the first type of the C-CDA standard, initiating a document conversion process comprising:
scanning the first document, the scanned first document comprising a plurality of patient information fields;
determining whether any of the plurality of patient information fields in the scanned first document comprise a reportable condition; and
in response to determining that at least one patient information field of the plurality of patient information fields comprises the reportable condition, generating, using the first document, a second document associated with a second type of the C-CDA standard and comprising the reportable condition by:
identifying, from a first portion of the plurality of patient information fields in the scanned first document, required patient information, the required patient information required for inclusion in documents associated with the second type of the C-CDA standard;
identifying, from a second portion of the plurality of patient information fields in the scanned first document, unnecessary patient information, the unnecessary patient information specified by the second type of the C-CDA to be omitted from documents associated with the second type of the C-CDA standard; and
generating the second document by populating required fields specified by the second type of the C-CDA standard with the required patient information identified from the first portion of the plurality of patient information fields in the scanned first document and omitting populating the second document with the unnecessary patient information identified from the second portion of the plurality of patient information fields; and
when the first document is not associated with the first type of the C-CDA, rejecting the first document,
wherein the second type of the C-CDA standard is different than the first type of the C-CDA standard, and wherein the generated second document associated with the second type of the C-CDA standard is encoded and specifically formatted for electronic ingestion by a public health agency (PHA) computing device associated with a PHA to identify the reportable condition in the second document.

15. The system of claim 14, wherein the operations further comprise, after generating the second document, transmitting electronically the second document automatically to the PHA computing device associated with the PHA, the PHA computing device configured to process the second document to extract the reportable condition from the second document.

16. The system of claim 14, wherein the first type of the C-CDA standard comprises a Continuity of Care Document (CCD) generated by an electronic health record (EHR) system, the EHR system configured to:
receive the patient information from a HCP device associated with the patient, the patient information input to the HCP device by the HCP; and
generate the CCD based on the received patient information.

17. The system of claim 14, wherein the first type of the C-CDA standard comprises a patient care document generated by an electronic health record (EHR) system, the EHR system configured to:
receive the patient information from a HCP device associated with the patient, the patient information input to the HCP device by the HCP; and
generate the patient care document based on the received patient information.

18. The system of claim 14, wherein the second type of the C-CDA standard comprises an Electronic Initial Case Report (eICR).

19. The system of claim 14, wherein the operations further comprise:
determining that the second type of the C-CDA standard specifies one or more fields to be created in documents associated with the second type of the C-CDA standard; and
for each such field:
based on metadata of the first document, determining from a third portion of the plurality of patient information fields in the scanned first document, whether corresponding optional patient information exists for inclusion in the corresponding field; and one of
when the corresponding optional patient information exists, populating the corresponding field specified by the second type of the C-CDA standard with the corresponding optional patient information; or
when the corresponding optional patient information does not exist, populating the corresponding field specified by the second type of the C-CDA standard with blank data.

20. The system of claim 14, wherein determining whether any of the plurality of patient information fields in the scanned first document comprise the reportable condition comprises:
obtaining a list of reportable conditions from a reportable condition datastore in communication with the data processing hardware, the list of reportable conditions specified by the PHA; and
determining that the at least one patient information field of the plurality of patient information fields comprises one of the reportable conditions in the list of reportable conditions obtained from the reportable condition datastore.

21. The system of claim 14, wherein the at least one patient information field of the plurality of patient information fields comprises the reportable condition when the at least one patient information field comprises a diagnoses code indicative of the reportable condition.

22. The system of claim 14, wherein the at least one patient information field of the plurality of patient information fields comprises the reportable condition when the at least one patient information field comprises a laboratory code indicative of the reportable condition.

23. The system of claim 22, wherein the laboratory code indicative of the reportable condition comprises a Laboratory Observation Identifiers Names and Codes (LOINC) code.

24. The system of claim 14, wherein the at least one patient information field of the plurality of patient information fields comprises the reportable condition when the at least one patient information field comprises a Systematized Nomenclature of Medicate (SNOMED) code indicative of the reportable condition.

25. The system of claim 14, wherein the operations further comprise, prior to generating the second document associated with the second type of the C-CDA standard:
determining whether any of the plurality of patient information fields in the scanned first document are missing corresponding required patient information required for generating documents associated with the second type of the C-CDA standard; and
when one or more of the plurality of patient information fields in the scanned first document are missing the corresponding required patient information, ceasing the generating of the second document associated with the second type of the C-CDA standard.

26. The system of claim 14, wherein the operations further comprise, when none of the plurality of patient information fields in the scanned first document comprise the reportable condition, forgoing the generating of the second document associated with the second type of the C-CDA standard using the first document.

* * * * *